United States Patent [19]

Matsuda et al.

[11] Patent Number: 5,907,051

[45] Date of Patent: May 25, 1999

[54] CATALYST AND METHOD FOR PRODUCING CARBONIC DIESTERS

[75] Inventors: Hirokazu Matsuda; Shingo Oda; Mitsuru Ohno, all of Himeji, Japan

[73] Assignee: Daicel Chemical Industries, Ltd., Sakai, Japan

[21] Appl. No.: 08/172,097

[22] Filed: Dec. 23, 1993

[30] Foreign Application Priority Data

Dec. 24, 1992 [JP] Japan .................................. 4-344167
Apr. 22, 1993 [JP] Japan .................................. 5-120732

[51] Int. Cl.$^6$ ..................................................... C07C 69/96
[52] U.S. Cl. ........................... 558/270; 558/274; 558/277
[58] Field of Search ................................. 558/277, 270, 558/274; 502/180, 416

[56] References Cited

U.S. PATENT DOCUMENTS

| | | | |
|---|---|---|---|
| 3,639,266 | 2/1972 | Battista | 252/421 |
| 3,950,267 | 4/1976 | Arakawa et al. | 252/425 |
| 4,625,044 | 11/1986 | Curnutt | |
| 5,004,827 | 4/1991 | Curnutt | 558/277 |
| 5,142,086 | 8/1992 | King, Jr. et al. | 558/274 |

FOREIGN PATENT DOCUMENTS 523728   1/1993   European Pat. Off. .

OTHER PUBLICATIONS

WO 87/07601—Dec. 17, 1987.

*Primary Examiner*—Marianne M. Cintins
*Assistant Examiner*—Dwayne C. Jones
*Attorney, Agent, or Firm*—Cushman, Darby & Cushman IP Group of Pillsbury Madison & Sutro LLP

[57] ABSTRACT

A method of producing a carbonic diester involves allowing an alcohol to react with carbon monoxide and oxygen in the presence of a supported catalyst wherein the support is an activated carbon obtained from a vegetable or polymeric raw material, a support having an aluminum content of up to 2% by weight, or a support having sulfur content of up to 1% by weight.

25 Claims, No Drawings

5,907,051

CATALYST AND METHOD FOR PRODUCING CARBONIC DIESTERS

FIELD OF THE INVENTION

The present invention relates to a catalyst for synthesizing a carbonic diester and to a method of producing a carbonic diester which comprises allowing the corresponding alcohol to react with carbon monoxide and oxygen in the presence of said catalyst.

BACKGROUND OF THE INVENTION

Carbonic diesters are compounds of value as automotive gas additives and organic solvents or as reactants, replacing phosgene, in the production of various carbonates, carbamates, urethanes and fine chemicals such as drugs and agrochemicals.

For the commercial production of a carbonic diester, generally the corresponding alcohol is allowed to react with phosgene. However, this known technology demands the use of phosgene having a great toxic potential and, moreover, the reaction of the alcohol with phosgene gives rise to a large quantity of hydrochloric acid which is a highly corrosive substance.

Therefore, a technology has been proposed for producing a carbonic diester without the use of phosgene which comprises allowing the corresponding alcohol to react with carbon monoxide and oxygen in the presence of a catalyst. The catalyst used for this purpose can be classified into two major categories, i.e. the palladium catalyst including a compound of palladium as the main catalyst component and the copper catalyst including a compound of copper as the main catalyst component.

The liquid-phase reaction using the palladium catalyst is described in Japanese Patent Publication Nos. 8816/1986 and 43338/1986. According to this technology, a palladium compound as the main catalyst component is used in combination with a copper compound and an alkali metal compound. The liquid phase reaction conducted in the presence of a copper catalyst is described in Japanese Patent Publication No. 8020/1981. However, since the reaction system containing such a catalyst, irrespective of whether it is a palladium catalyst or a copper catalyst, is highly corrosive, the reaction must be conducted in a pressure-resistant reactor having an anticorrosive lining made of e.g. glass or a baked-on type enamel. Therefore, since there is an upper limit to the size of a pressure-resistant reactor having such an anticorrosive lining that can be fabricated, it is difficult to produce a carbonic diester containing such a catalyst on a commercial scale.

To obviate this corrosion problem associated with a liquid-phase reaction, a technology has been proposed for producing a carbonic diester which comprises allowing the corresponding alcohol to react with carbon monoxide and oxygen in a gas phase in the presence of a solid catalyst. For example, U.S. Pat. No. 4,625,044 discloses a catalyst comprising a complex formed with copper hydrocarbyloxy halide supported on an activated carbon for a reaction in a gas phase. JP-A-503460/1988 corresponding to WO87/07601 based on U.S. Ser. No. 871,725 (filed on Jun. 6, 1986) discloses a production process which comprises allowing all the reactants to react in a gas phase using a catalyst comprising metal halide supported on a solid support by an impregnation technique. In these literatures, an activated carbon especially an activated carbon derived from lignite, a kind of mineral substance, which have been acid washed is used in order to obtain a high reaction rate. Further, above-mentioned U.S. Pat. No. 4,625,044 teaches that a particularly preferred activated carbon is a Darco (trade name, ICI Americas, Inc.), as an acid washed activated carbon derived from lignite.

Further, G. L. Curnutt, who is the inventor of U.S. Pat. No. 4,625,044 and JP-A-503460/1988 mentioned above, reported in American Chemical Society concerning the catalytic activity in a gas-phase reaction in the presence of solid catalysts using activated carbon as a support, wherein lignite, bituminous coal, peat, petroleum coke and the like was used as the raw material of the activated carbon.

According to these technologies, however, a suffiient catalytic activity and selectivity of the reacion for the objective carbonic diester are not yet obtained, thus, production of the same in a good yield and with high selectivity has not been achieved.

SUMMARY OF THE INVENTION

Accordingly, the object of the present invention is to provide a catalyst for synthesizing a carbonic diester having a high catalytic activity and reaction selectivity.

It is another object of the invention to provide a commercial method wherein a carbonic diester can efficiently be produced, being conducive to high production, and capable of providing with a high selectivity for the carbonic diester.

After a great research effort concerning a kind of activated carbon as a support of a solid catalyst and the effects of an aluminum content or a sulfur content of the support on the reaction, to accomplish the above-mentioned objects, the inventors of the present invention discovered that when an activated carbon obtained from a vegetable or polymer raw material, or a support wherein a content of aluminium or sulfur is little is used as said support, carbonic diesters can be produced in a good yield and with a high selectivity. Thus, the present invention was accomplished.

Accordingly, this invention provides (1) a catalyst for synthesizing a carbonic diester comprising a catalyst component supported on a support wherein the support is (i) an activated carbon obtainable from a vegetable raw material or polymer raw material. The present invention also provides (2) a catalyst for synthesizing a carbonic diester comprising a catalyst component supported on a support wherein the support is (ii) a support having an aluminium content of 2% by weight or less, and (3) a catalyst for synthesizing a carbonic diester comprising a catalyst component supported on a support wherein the support is (iii) a support having a sulfur content of 1% by weight or less.

The catalyst component may include copper compounds and the like. Carbonizable vegetable raw materials, carbonizable polymers including thermosetting resins, thermoplastic resins and so on can be used as the raw material of the activated carbon. The support having the aluminium content of 2% by weight or less and the sulfur content of 1% by weight or less can be preferably employed.

The present invention also provides a method of producing a carbonic diester which comprises allowing an alcohol to react with carbon monoxide and oxygen in the presence of said catalyst.

An alcohol having about 1 to 6 carbon atoms can be used. The reaction can be carried out at the temperature of 20 to 200° C. and under the pressure of 1 to 200 atm.

DETAILED DESCRIPTION OF THE INVENTION

It should be understood that the terms "aluminum content" and "sulfur content" as used in this specification mean the amounts of aluminum component and sulfur component respectively contained in a support (carrier), in terms of atomic aluminium or sulfur. The aluminium content and sulfur content may be determined by, for example, atomic absorption analysis and so on. In the contents mentioned above, the term "0% by weight" means that the content is less than the limit of detection by the atomic absorption analysis.

The catalyst component mentioned above may be virtually any catalyst component for oxidative carbonylation, thus including transition metals such as copper, iron, nickel, cobalt, palladium, platinum, rhodium, iridium, ruthenium; and compounds containing these transition metals.

As the compounds containing the transition metals, there may be mentioned, for example, halides such as fluoride, chloride, bromide and iodide; salts with an inorganic acid such as nitric acid, carbonic acid, boric acid, phosphoric acid and the like; salts with an organic acid such as formic acid, acetic acid, propionic acid, pivalic acid, oxalic acid, malonic acid, lactic acid, malic acid, citric acid, tartaric acid, benzoic acid, toluic acid, salicylic acid, phthalic acid, nicotinic acid and so on; salts of an oxo acid of metal such as vanadic acid, stannic acid, antimonic acid, bismuthic acid molybdic acid, tungstic acid and the like; oxides; hydroxides; salts of phenols such as phenoxide; complexes each formed between one of these metal-containing compounds and a ligand component and so on.

The examples of the ligand component include amines such as ethylenediamine; a nitrogen-containing heterocyclic compound such as imidazole and pyridine; an organophosphorus compound such as triphenylphosphine and trimethylphosphite; nitriles such as benzonitrile; isonitriles; phosphorus amides such as hexamethylphosphorus triamide and the like. The ligand compound may be used in a proportion of, for example, about 0.1 to 10 moles per mole of said metal-containing compound.

From the standpoints of catalytic activity, selectivity of reaction, catalyst life and others, copper compounds are preferred to be employed among these catalyst components. Practically preferred embodiments of the copper compounds include, for example, cuprous halides such as cuprous fluoride, cuprous chloride, cuprous bromide and cuprous iodide; cupric halides such as cupric fluoride, cupric chloride, cupric bromide and cupric iodide; salts of copper with an inorganic weak acid such as copper borate; salts of copper with an organic acid such as copper acetate and copper oxalate; complexes each formed with one of these compounds such as an amine complex, amide complex, a complex formed with a nitrogen-containing heterocyclic compound, phosphine complex, phosphite complex, nitrile complex, isonitrile complex, phosphorus amide complex and the like. The practically preferred examples of the catalyst component include, among others, copper chloride such as cuprous chloride and cupric chloride and complexes each formed with one of these copper chlorides.

The above-mentioned catalyst components can be used independently or in combination. Examples of the usage of the catalyst components in combination include a combination of the copper-containing compound and a metal of the platinum group such as palladium, platinum and rhodium, a compound containing a metal of the platinum group or others.

The compound containing a metal of the platinum group includes, for example, a salt with an inorganic acid, a salt with an organic acid, an oxide, a hydroxide and the like as mentioned above. The amount of the metal of the platinum group or the compound containing the said metal for use is voluntarily selected as far as considering catalytic activity, economical performance and the like. However, from the standpoints that the platinum group metals or compounds containing these metals show an effect even when used in a small amount and that these metals or compounds are expensive in general, the using amount of said metal or compound per mole of the copper-containing compound is usually about 1 mole or less, preferably about 0.1 mole or less and more preferably about 0.0001 to 0.05 mole.

The catalyst component can also be used in combination with an alkali metal compound such as lithium chloride, sodium chloride and potassium fluoride; an alkali earth metal compound such as magnesium chloride, calcium chloride and strontium bromide; boric acid or salts of boric acid; and the like.

It is an outstanding characteristic of the above-mentioned catalyst (1) of the present invention that an activated carbon obtained from a vegetable or polymer raw material is employed as the support (i) of the catalyst.

The vegetable (plant) raw material includes, for instance, carbonizable vegetable or plant raw materials such as wood, sawdust, charcoal, vegetable seed shells such as coconut shells and walnut shells, seeds of fruits, lignin, by-products in pulp production, waste materials in sugar refining, blackstrap molasses; carbonized products of these materials; and so on.

As examples of said polymer raw material, there may be mentioned carbonizable polymers including thermosetting resins such as phenol resin, furan resin, epoxy resin and the like; thermoplastic resins such as acrylic resin, polyacrylonitrile, vinylidene chloride resin and so on; rayon; cellulose; and the like.

Among these raw materials, carbonizable seed shells such as coconut shells, and carbonized or graphatized products thereof; carbonizable polymers including thermosetting resins such as phenol resin, furan resin and epoxy resin, thermoplastic resins and so on can preferably be used.

Generally, an activated carbon produced by using a mineral raw material, a mining product, such as peat, grass peat, lignite (lignite, brown coal), bituminous coal, anthracite, coke, coal tar, petroleum, coal pitch, residues in petroleum distillation and petroleum pitch frequently contains impurities such as silicon, aluminium, phosphorus, sulfur, chlorine, potassium, calcium, iron, titanium, sodium, magnesium and so on. For instance, as described in JP-A-503460/1988 mentioned above, the activated carbon produced by using lignite as raw material contains a large amount of impurities such as aluminium, silicon, sulfur and the like, and even after washed with an acid, the aluminium content is usually more than 2% by weight and the sulfur content is usually more than 1% by weight.

On the contrary, the activated carbon obtained from the above mentioned vegetable or polymer raw material, namely non-mineral raw material, contains said impurities in a diminished proportion. It may be for this reason that when use is made of the activated carbon obtained from the vegetable or polymer raw material as the support of a solid support catalyst, a high catalytic activity and selectivity of reaction can be realized.

The aluminium content of said activated carbon is, for example, about 2% by weight or less, preferably about 0 to 1% by weight, more preferably about 0 to 0.1% by weight, and for still better results, about 0 to 0.05% by weight. The sulfur content of the activated carbon is, for example, about 1% by weight or less, preferably about 0 to 0.7% by weight, more preferably about 0 to 0.5% by weight, and for still better results, about 0 to 0.3% by weight.

An activated carbon is generally produced by gasactivation method comprising activating a carbonized and graded carbonaceous raw material with steam, air (oxygen) and a combustion gas (carbon dioxide), by chemical-activation method comprising impregnating a raw material with an aqueous solution of zinc chloride or the like and calcining the same to carbonize or graphitize, or other techniques. The activated carbon of the present invention can be produced by means of any one of these methods.

The activated carbon may have any form, for example powdery, granular, fibrous structure, pellet structure, honeycomb structure or the like.

The mean pore size of the activated carbon can be any size within the range wherein the catalytic activity is not adversely affected. As such, the mean pore size may, for example, be about 10 to 100 Å and preferably about 10 to 50 Å. The reaction rate tends to be significantly lowered when the mean pore size is less than 10 Å. Conversely, the catalyst life has a tendency to be shortened when the mean pore size exceeds 100

The specific surface area of the activated carbon is usually about 50 $m^2/g$ or more, preferably about 500 $m^2/g$ or more, and more preferably about 700 to 3000 $m^2/g$. When the specific surface area is less than 50 $m^2/g$, the catalytic activity has a tendency to decrease.

It is an important characteristic of the above-mentioned catalyst (2) of the present invention that a support (ii) wherein the aluminium content is 2% by weight or less is used as a support of the catalyst. An outstanding characteristic of the above-mentioned catalyst (3) of the invention is that a support (iii) having the sulfur content of 1% by weight or less is used as a support of the catalyst.

The aluminium content in the support of the catalyst (2) is preferably about 0 to 1% by weight, more preferably about 0 to 0.1% by weight, and particularly preferred is about 0 to 0.05% by weight. The sulfur content in the support of the catalyst (3) is preferably about 0 to 0.7% by weight, more preferably about 0 to 0.5% by weight, and specifically preferred is about 0 to 0.3% by weight.

Among these supports of the catalysts (2) and (3), the preferable example of the support includes a support having the aluminium content of 2% by weight or less as well as the sulfur content of 1% by weight or less.

The catalytic activity and the reaction selectivity, among them, the methanol-based selectivity for the carbonic diester, decrease significantly when the aluminium content exceeds 2% by weight or the sulfur content exceeds 1% by weight in the support respectively. Its reason may be understood because aluminium or an aluminium-containing compound, and sulfur or a sulfur-containing compound inhibit the producing reaction of the desired carbonic diester with side reactions being promoted.

The support of the catalysts (2) and (3) can be selected within the range wherein the catalytic reaction is not adversely affected, thus, including an activated carbon, titania, vanadia, zirconia and so on. Activated carbon is practically preferred among these supports.

The raw material of the activated carbon used as the supports of the catalysts (2) and (3) is not critical and can be any one of the vegetable, mineral or polymer raw material as mentioned above.

As described above, generally, an activated carbon produced by using a mineral raw material frequently contains aluminium and sulfur in large proportions. Sulfur may be found in the activated carbon in the form of sulfonic acid, salts of sulfonic acid, sulfuric acid, salts of sulfuric acid or the like. In such cases, the aluminium content and sulfur content can be reduced 2% by weight or less, and 1% by weight or less respectively as prescribed above, by refining the raw material or conducting a suitable treatment in the production procedure of the activated carbon.

The treatment for reducing the aluminium content is exemplified as high-temperature chlorination and the like. The high-temperature chlorination may be conducted, for instance, by treating a raw material or intermediate of the activated carbon or the activated carbon itself with a gas containing chlorine at a temperature of about 300 to 500° C., and, if necessary, washing the same with water. The high-temperature chlorination can be carried out at any process of the production, for example, a step for preparing raw materials, pretreatment process, activation process, after-treatment process and the like.

As examples of the treatment for reducing the sulfur content, there may be mentioned alkali washing and so on. The alkali washing can be carried out by treating a raw material or intermediate of the activate carbon, or the activated carbon itself with an alkaline solution at a temperature of about 50 to 200° C., and, if required, washing with water. The alkaline solution is exemplified as an aqueous solution of a basic substance including, for example, hydroxides of alkali metal such as sodium hydroxide and potassium hydroxide; hydroxides of alkaline earth metal such as magnesium hydroxide and barium hydroxide; carbonates of alkali metal such as sodium carbonate and potassium carbonate; carbonates of alkaline earth metal such as magnesium carbonate and calcium carbonate; hydrogencarbonates of alkali metal such as sodium hydrogencarbonate; and the like. The alkali washing can be carried out at any one of the above mentioned production process.

The amount of the catalyst component of the catalysts (1) to (3) to be supported may vary usually about from 0.5 to 80% by weight, preferably about from 1 to 40% by weight, and more preferably around the saturated adsorption amount of the support, for instance, when an activated carbon is used, about from 2 to 20% by weight, respectively based on the weight of the support.

The catalysts (1) to (3) of the present invention can be prepared in a conventional manner such as impregnation, coating, spraying, adsorption, precipitation or other techniques. Such a technique wherein the catalyst component or precursor thereof can be supported on the support with a high dispersion is preferred to prepare the catalyst. Supporting of the catalyst component may be carried out in a single stage as well as in a multistage.

When use is made of a catalyst component soluble in a solvent, e.g. water, such as copper acetate or palladium acetate to be supported, the catalyst component as a solution can be used to be supported.

When a catalyst component being slightly or sparingly soluble in a solvent such as copper borate, copper phosphate, copper oxalate, copper hydroxide or others is employed, said catalyst component can be supported on a support in the form of a combination of two or more soluble compounds corresponding to the precursors of said catalyst component. For instance, supporting can be conducted using a combination of copper sulfate and sodium borate, copper sulfate and dipotassium hydrogenphosphate, copper nitrate and sodium oxalate, copper sulfate and sodium hydroxide, or other combinations.

Further, the catalyst supporting an oxide such as copper oxide can be prepared as follows. First, a salt of metal corresponding to said oxide is supported on a support, and the resulting substance may be treated with a high concentration and excess amount of sodium hydroxide, or dried and calcined. When a plural of the catalyst components are used, they may be supported simultaneously, or in turn.

The solvent mentioned just above as employed to support the catalyst component on a support includes, among others, water; ketones such as acetone, methyl ethyl ketone and cyclohexanone; ethers such as diethyl ether, dibutyl ether, dimethoxyethane, dioxane and tetrahydrofuran; carboxylic acids such as formic acid, acetic acid and propionic acid; esters of carboxylic acids such as methyl acetate, ethyl acetate, isopropyl acetate, butyl acetate, amyl acetate, cellosolve acetate and ethyl propionate; amides of carboxylic acids such as N,N-dimethylformamide; nitriles such as acetonitrile, propionitrile and benzonitrile; aliphatic hydrocarbons such as hexane and octane; alicyclic hydrocarbons such as cyclohexane; aromatic hydrocarbons such as benzene, toluene, xylene and ethyl benzene; halogenated hydrocarbons such as carbon tetrachloride, chloroform, dichloromethane and 1,2-dichloroethane; the objective carbonic diester; and the like. These solvents can be used independently or in combination.

After supporting the catalyst component on the support, the resulting catalyst can also be molded into a suitable structure, for example, orbicular, cylindrical, multilateral pillar or honeycomb forms, according to the kind of reactor, reaction or other conditions.

In the catalyst of the present invention, the catalyst component is supported on an activated carbon obtained from the vegetable or polymer raw material, or a support wherein the aluminium content or the sulfur content is low. Thus, the catalytic activity of the catalyst is remarkably high with side reactions being significantly inhibited. Therefore, when said catalyst is employed, the desired carbonic diester can be produced with a high yield and selectivity by allowing the corresponding alcohol to react with carbon monoxide and oxygen.

According to the method of producing a carbonic diester of the present invention, in the presence of said catalyst, an alcohol is allowed to react with carbon monoxide and oxygen.

The examples of the alcohol mentioned above include saturated aliphatic alcohols such as methanol, ethanol, 1-propanol, 2-propanol and 1-butanol; unsaturated aliphatic alcohols such as allyl alcohol; alicyclic alcohols such as cyclohexanol; aromatic alcohols such as benzyl alcohol and phenol; and polyhydric alcohols such as ethylene glycol and polyethylene glycol. The term "aromatic alcohol" is used herein to include a variety of phenols containing a phenolic hydroxyl group.

The preferred alcohol is a saturated or unsaturated monohydric alcohol, such as alcohols of about 1 to 6 carbon atoms. The particularly preferred alcohol includes methanol and ethanol, with methanol being the alcohol of choice.

Carbon monoxide and oxygen as reactants need not be a high-purity gas but can be used as diluted with an inert gas such as nitrogen, argon, helium, carbon dioxide and so on. In such cases, air may be substituted for oxygen. Furthermore, carbon dioxide gas as a by-product formed in the course of reaction may be recycled in the reaction system.

The producing method of the present invention can be applied to any of a liquid-phase reaction or gas-phase reaction.

When the carbonic diester is produced by a liquid-phase reaction, the reaction may be conducted in the absence of a solvent or in the presence of an inert solvent. The amount of the catalyst to be used can be selected from the range depending on reaction velocity, simplicity of operation of after-treatment and economic factors. Thus, the proportion of the catalyst in the reaction solution or suspension is, for example, about 0.001 to 5 g atoms/liter, preferably about 0.01 to 3 g atoms/liter and more preferably about 0.1 to 2.5 g atoms/liter, in terms of atomic metal.

The reaction temperature may range usually about from 20 to 200° C. and preferably about from 80 to 150° C. When the reaction temperature is excessively low, the reaction rate may be significantly lowered, on the contrary, when the reaction temperature is excessively high, it gives rise to side reactions.

The reaction pressure is generally about 1 to 200 atm and preferably about 1 to 60 atm, and the carbon monoxide partial pressure is, for instance, about 0.1 to 200 atm and preferably about 1 to 60 atm. The oxygen partial pressure is not critical but is generally selected from the range where an explosive mixture will not be formed. Thus, the oxygen partial pressure may for example be generally about 0.1 to 20 atm and preferably about 0.5 to 10 atm.

On the contrary, the method of producing a carbonic diester by gas-phase reaction can be carried out into practice using a fixed-bed reactor, fluidized-bed reactor, moving-bed reactor or other reactors. The structure of the catalyst is not critical. When a fixed-bed reactor is employed in the reaction, however, from viewpoints to reduce pressure loss of the reaction gases and to remove reaction heat, a catalyst in granular or pellet form is preferably used. Conversely, when the reaction is conducted using a fluidized-bed reactor or moving-bed reactor, a powdered catalyst is so preferred to be employed that the catalyst particles can easily be fluidized with gas stream.

The gas-phase reaction can be carried out at the reaction temperature of usually about 50 to 200° C., at the reaction pressure of usually about 1 to 50 atm and with the space velocity of the material gas of, for example, about 10 to 100000 $h^{-1}$ and preferably about 100 to 10000 $h^{-1}$. Regarding the composition of the feed gas flow to the reactor, the alcohol content may be about 1 to 50% by volume and the carbon monoxide content may vary about from 40 to 95% by volume, respectively based on the total volume of the alcohol, carbon monoxide and oxygen. The amount of carbon monoxide per mole of the alcohol to be employed is usually about 0.1 to 1000 moles and preferably about 0.2 to 100 moles. The using amount of oxygen per mole of the alcohol is usually about 0.001 to 2 moles and preferably about 0.01 to 1.5 moles.

The method of the invention can be conducted in practice by any system selected from a batch system, semi-batch system or continuous system. The desired carbon diester corresponding to the material alcohol can be obtained by treating resulting products in a conventional manner.

Thus, the catalyst for synthesizing a carbonic diester of the present invention has a high catalytic activity and reaction selectivity.

In accordance with the method of the invention wherein the reaction is conducted using such an excellent catalyst as mentioned above, carbonic diester can be produced with a commercial efficiency as well as good yield and high selectivity.

The following examples are intended to describe the present invention in further detailed and should by no means be interpreted as defining the scope of the invention.

EXAMPLES

Example 1 (Cuprous chloride catalyst)

Using acetonitrile as the solvent, 1.9 g of cuprous chloride was supported on 40 g of activated carbon obtained from coconut shells (trade name: Granular Shirasagi C2X 4/6-2, aluminium content 0.005% by weight; sulfur content 0.18% by weight; Takeda Chemical Industries, Ltd.) in the conventional manner and the resulting catalyst was dried at 130° C. under reduced pressure.

The supported catalyst thus obtained was packed into a stainless steel tubular reactor, 27 mm in inside diameter and 450 mm long, to provide a 35 mm-deep catalyst bed. With the reaction temperature being set at 120° C. and the internal pressure of the reactor held at 7 $Kg/cm^2$ gauge, the reactor was supplied with 43.2 normal liters/h of carbon monoxide gas, 1.74 normal liters/h of oxygen gas and 8.20 normal liters/h (11.7 g/h) of methanol, thus the reaction was conducted for 4 hours.

The resulting products obtained within the time course of three hours to four hours from the initial of the reaction were respectively analyzed by gas chromatography.

As a result, 9.1% by molar of the feed methanol was transformed to dimethyl carbonate. The carbon monoxide-based selectivity for dimethyl carbonate was 73% and the methanol-based selectivity for dimethyl carbonate was 98%. Dimethyl carbonate was produced at a rate of 0.80 mole/h per liter of the catalyst layer.

Example 2 (Cuprous chloride catalyst)

The supported catalyst prepared in the same manner as in Example 1 was packed into a stainless steel tubular reactor, 27 mm in inside diameter and 450 mm long, to provide a 69 mm-deep catalyst bed. With the reaction temperature being set at 120° C. and the internal pressure of the reactor held at 20 $Kg/cm^2$ gauge, the reactor was supplied with 153 normal liters/h of carbon monoxide gas, 2.1 normal liters/h of oxygen gas and 10.0 normal liters/h (14.3 g/h) of methanol, thus the reaction was carried out for 4 hours.

The resulting products obtained within the time course of three hours to four hours from the initial of the reaction were respectively analyzed by gas chromatography.

As a result, 20% by molar of the feed methanol was transformed to dimethyl carbonate. The carbon monoxide-based selectivity for dimethyl carbonate was 60% and the methanol-based selectivity for dimethyl carbonate was 98%. Dimethyl carbonate was produced at a rate of 0.78 mole/h per liter of the catalyst layer.

Example 3 (Cuprous chloride catalyst)

Using acetonitrile as the solvent, 2.9 g of cuprous chloride was supported on 40 g of activated carbon obtained from phenol resin (trade name: Kuraray-coal BP25; aluminium content less than 1 ppm (by weight); sulfur content 0.04% by weight; Kuraray Chemical, Co., Ltd.) in the conventional manner and was dried at 130° C. under reduced pressure. In this example, considering the bulk density of the activated carbon, the supporting amount of cuprous chloride was so selected as the amount of copper atom per unit volume of the catalyst being the same as that of Example 1.

Using the catalyst obtained above, the reaction procedure of Example 1 is otherwise repeated. The resulting products obtained within the time course of three hours to four hours from the initial of the reaction were respectively analyzed by gas chromatography.

As a result, 8.0% by molar of the feed methanol was transformed to dimethyl carbonate. The carbon monoxide-based selectivity for dimethyl carbonate was 91% and the methanol-based selectivity for dimethyl carbonate was 99%. Dimethyl carbonate was produced at a rate of 0.74 mole/h per liter of the catalyst layer.

Example 4 (Cuprous chloride catalyst)

The reaction procedure of Example 2 was repeated except for using the catalyst prepared in the same manner as in Example 3.

The resulting products obtained within the time course of three hours to four hours from the initial of the reaction were respectively analyzed by gas chromatography.

As a result, 27% by molar of the feed methanol was transformed to dimethyl carbonate. The carbon monoxide-based selectivity for dimethyl carbonate was 65% and the methanol-based selectivity for dimethyl carbonate was 100%. Dimethyl carbonate was produced at a rate of 1.05 mole/h per liter of the catalyst layer.

Example 5 (Cuprous chloride catalyst)

Cuprous chloride (1.9 g) was supported on 40 g of crushed activated carbon obtained from coconut shells (trade name: LH2C 20/48, Takeda Chemical Industries, Ltd.) using acetonitrile as the solvent and resulting activated carbon was dried at 130° C. under reduced pressure.

Except for using the supported catalyst thus obtained above, the reaction procedure of Example 1 was repeated. The resulting products obtained within the time course of three hours to four hours from the initial of the reaction were respectively analyzed by gas chromatography.

As a result, 7.2% by molar of the feed methanol was transformed to dimethyl carbonate. The carbon monoxide-based selectivity for dimethyl carbonate was 100% and the methanol-based selectivity for dimethyl carbonate was 97%. Dimethyl carbonate was produced at a rate of 0.68 mole/h per liter of the catalyst layer.

Example 6 (Cuprous chloride catalyst)

Cuprous chloride (1.9 g) was supported on 40 g of activated carbon obtained from coconut shells (trade name: Tsurumicoal 4GV, Tsurumicoal Co., Ltd.) using acetonitrile as the solvent and the resulting activated carbon was dried at 130° C. under reduced pressure.

The reaction was conducted in the same manner as in Example 1, except for using the supported catalyst thus obtained above. The resulting products obtained within the time course of three hours to four hours from the initial of the reaction were respectively analyzed by gas chromatography.

As a result, 9.8% by molar of the feed methanol was transformed to dimethyl carbonate. The carbon monoxide-based selectivity for dimethyl carbonate was 80% and the methanol-based selectivity for dimethyl carbonate was 98%. Dimethyl carbonate was produced at a rate of 0.91 mole/h per liter of the catalyst layer.

Example 7 (Cuprous chloride catalyst)

On 40 g of activated carbon obtained from coconut shells (trade name: Maxsorve, Kansai Thermochemical Co., Ltd), was supported 2.3 g of cuprous chloride and the resulting activated carbon was dried at 130° C. under reduced pressure.

The reaction procedure of Example 1 was repeated except for using the supported catalyst thus obtained above. The resulting products obtained within the time course of three hours to four hours from the initial of the reaction were respectively analyzed by gas chromatography.

As a result, 7.9% by molar of the feed methanol was transformed to dimethyl carbonate. The carbon monoxide-based selectivity for dimethyl carbonate was 82% and the methanol-based selectivity for dimethyl carbonate was 97%. Dimethyl carbonate was produced at a rate of 0.73 mole/h per liter of the catalyst layer.

Comparative Example 1 (Cuprous chloride catalyst)

Using acetonitrile as the solvent, 2.2 g of cuprous chloride was supported on 40 g of lignite activated carbon washed with acid (trade name: DARCO 12-20; aluminium content 2.10% by weight; sulfur content 1.22% by weight; Aldrich Co., Ltd.) and resulting activated carbon was dried at 130° C. under reduced pressure.

Using the supported catalyst thus obtained, the reaction procedure of Example 1 was repeated otherwise. The resulting products obtained within the time course of three hours to four hours from the initial of the reaction were respectively analyzed by gas chromatography.

As a result, 4.4% by molar of the feeded methanol was transformed to dimethyl carbonate. The carbon monoxide-based selectivity for dimethyl carbonate was 88% and the methanol-based selectivity for dimethyl carbonate was 92%. Dimethyl carbonate was produced at a rate of 0.41 mole/h per liter of the catalyst layer.

Comparative Example 2 (Cuprous chloride catalyst)

In an aqueous solution of aluminium nitrate, was dipped 40 g of activated carbon obtained from coal (trade name: Taiko GL30, Futamura Chemical Industries, Ltd.) and prescribed amount of aluminium nitrate was impregnated on the activated carbon to prepare a activated carbon containing 3.1% by weight of aluminium. On the activated carbon thus obtained, was supported 2.2 g of cuprous chloride using acetonitrile as the solvent, and supported activated carbon was dried at 130° C. under reduced pressure.

The reaction was conducted in the same manner as in Example 1, except for using the supported catalyst thus obtained. The resulting products obtained within the time course of three hours to four hours from the initial of the reaction were respectively analyzed by gas chromatography.

As a result, 3.2% by molar of the feeded methanol was transformed to dimethyl carbonate. The carbon monoxide-based selectivity for dimethyl carbonate was 75% and the methanol-based selectivity for dimethyl carbonate was 88%. Dimethyl carbonate was produced at a rate of 0.30 mole/h per liter of the catalyst layer.

Comparative Example 3 (Cuprous chloride catalyst)

The same activated carbon as used in Comparative Example 2 (40 g) was dipped in an aqueous solution of sulfuric acid and prescribed amount of sulfuric acid was impregnated on the same to prepare an activated carbon containing 2.0% by weight of sulfur.

On the activated carbon thus obtained, 2.2 g of cuprous chloride was supported and resulting activated carbon was dried at 130° C. under reduced pressure.

The reaction procedure of Example 1 was repeated except for using the supported catalyst thus obtained above. The resulting products obtained within the time course of three hours to four hours from the initial of the reaction were respectively analyzed by gas chromatography.

As a result, 2.9% by molar of the feeded methanol was transformed to dimethyl carbonate. The carbon monoxide-based selectivity for dimethyl carbonate was 72% and the methanol-based selectivity for dimethyl carbonate was 89%. Dimethyl carbonate was produced at a rate of 0.27 mole/h per liter of the catalyst layer.

Example 8 (Copper oxalate catalyst)

To an aqueous solution of 4.71 g of copper sulfate in 100 ml of water, the same activated carbon (40 g) as used in Example 1 was added to be supported copper sulfate thereon. The supported activated carbon was dried at 50° C. under reduced pressure and dipped in an aqueous solution of sodium oxalate being submitted to ion exchange, and the resulting activated carbon was washed with 1N aqueous solution of barium chloride as far as sulfuric acid radical was not detected. After dried under reduced pressure, the activated carbon was dried at 130° C. for 71 hours to prepare a catalyst supporting 3.0% by weight, as copper, of copper oxalate.

Using the supported catalyst obtained above, the reaction procedure of Example 1 was repeated otherwise. The resulting products obtained within the time course of three hours to four hours from the initial of the reaction were respectively analyzed by gas chromatography.

As a result, 4.2% by molar of the feeded methanol was transformed to dimethyl carbonate. Dimethyl carbonate was produced at a rate of 0.40 mole/h per liter of the catalyst layer.

Comparative Example 4 (Copper oxalate catalyst)

A catalyst supporting copper oxalate was prepared in the same manner as in Example 8, except for using the same activated carbon as in Comparative Example 1 and employing 5.45 g of copper sulfate.

The reaction procedure of Example 8 was repeated except that the supported catalyst thus obtained was employed. The resulting products obtained within the time course of three hours to four hours from the initial of the reaction were respectively analyzed by gas chromatography.

As a result, 2.8% by molar of the feeded methanol was transformed to dimethyl carbonate. The carbon monoxide-based selectivity for dimethyl carbonate was 71% and the methanol-based selectivity for dimethyl carbonate was 87%. Dimethyl carbonate was produced at a rate of 0.26 mole/h per liter of the catalyst layer.

Example 9 (copper borate catalyst)

Using an aqueous solution of sodium borate instead of aqueous solution of sodium oxalate, the supporting procedure of Example 8 was repeated otherwise to prepare a catalyst supporting 3.0% by weight, as atomic copper, of copper borate.

The reaction procedure of Example 1 was repeated except that the supported catalyst thus obtained was employed. The resulting products obtained within the time course of three hours to four hours from the initial of the reaction were respectively analyzed by gas chromatography.

As a result, 4.6% by molar of the feeded methanol was transformed to dimethyl carbonate. Dimethyl carbonate was produced at a rate of 0.43 mole/h per liter of the catalyst layer.

Comparative Example 5 (Copper borate catalyst)

Using the same activated carbon as in Comparative Example 1 and employing 5.45 g of copper sulfate, the supporting procedure of Example 9 was repeated otherwise to prepare a catalyst supporting copper borate.

The reaction was carried out in the same manner as in Example 9 except for using the supported catalyst thus obtained. The resulting products obtained within the time course of three hours to four hours from the initial of the reaction were respectively analyzed by gas chromatography.

As a result, 3.1% by molar of the feed methanol was transformed to dimethyl carbonate. The carbon monoxide-based selectivity for dimethyl carbonate was 69% and the methanol-based selectivity for dimethyl carbonate was 89%. Dimethyl carbonate was produced at a rate of 0.29 mole/h per liter of the catalyst layer.

Example 10 (Copper acetate catalyst)

In an aqueous solution of copper acetate, was dipped 40 g of the same activated carbon as used in Example 1 and was supported thereon 3.5 g of copper acetate. The supported activated carbon was dried at 130° C. under reduced pressure.

Using the supported catalyst thus obtained, the reaction procedure of Example 1 was repeated otherwise. The resulting products obtained within the time course of three hours to four hours from the initial of the reaction were respectively analyzed by gas chromatography.

As a result, 5.3% by molar of the feed methanol was transformed to dimethyl carbonate. The carbon monoxide-based selectivity for dimethyl carbonate was 45% and the methanol-based selectivity for dimethyl carbonate was 93%. Dimethyl carbonate was produced at a rate of 0.50 mole/h per liter of the catalyst layer.

Comparative Example 6 (Copper acetate catalyst)

The same activated carbon (40 g) as used in Comparative Example 1 was dipped in an aqueous solution of copper acetate to be supported thereon 4.0 g of copper acetate. The supported activated carbon was dried at 130° C. under reduced pressure.

The reaction procedure of Example 10 was repeated except for employing the supported catalyst thus obtained above. The resulting products obtained within the time course of three hours to four hours from the initial of the reaction were respectively analyzed by gas chromatography.

As a result, 2.8% by molar of the feed methanol was transformed to dimethyl carbonate. The carbon monoxide-based selectivity for dimethyl carbonate was 44% and the methanol-based selectivity for dimethyl carbonate was 80%. Dimethyl carbonate was produced at a rate of 0.26 mole/h per liter of the catalyst layer.

Comparative Example 7 (Copper acetate catalyst)

In an aqueous solution of copper sulfate, was dipped 40 g of the same activated carbon as used in Comparative Example 1 and 6.2% by weight of copper sulfate was supported thereon. The supported activated carbon was dried at 130° C. under reduced pressure, and was dipped in an aqueous solution of copper acetate to be supported thereon 4.0 g of copper acetate and dried at 130° C. under reduced pressure.

Using the supported catalyst obtained above, the reaction procedure of Example 10 was repeated otherwise. The resulting products obtained within the time course of three hours to four hours from the initial of the reaction were respectively analyzed by gas chromatography.

As a result, 0.8% by molar of the feed methanol was transformed to dimethyl carbonate. The carbon monoxide-based selectivity and methanol-based selectivity for dimethyl carbonate was not significantly determined, as the conversion of the raw materials being so small. Dimethyl carbonate was produced at a rate of 0.08 mole/h per liter of the catalyst layer.

What is claimed is:

1. A method of producing a carbonic diester which comprises allowing an aliphatic alcohol of 1 to 6 carbon atoms or an alicyclic alcohol of 3 to 6 carbon atoms to react with carbon monoxide and oxygen in the presence of a catalyst for synthesizing a carbonic diester consisting essentially of a copper compound as a catalyst component supported on a support, wherein said support is an activated carbon with a specific surface area of 700 to 3000 $m^2/g$ obtainable from a vegetable or polymer raw material and (i) said activated carbon is substantially free from aluminum or if it contains aluminum, the aluminum content of said activated carbon is greater than 0 up to 2% by weight, and (ii) said activated carbon is substantially free from sulfur or if it contains sulfur, the sulfur content of said activated carbon is greater than 0 up to 1% by weight.

2. The method of producing a carbonic diester according to claim 1 wherein the alcohol is methanol.

3. The method of producing a carbonic diester according to claim 1 wherein the reaction is conducted at the temperature of 20 to 200° C.

4. The method of producing a carbonic diester according to claim 1 wherein the reaction is conducted under the pressure of 1 to 200 atm.

5. The method of producing a carbonic diester according to claim 1 wherein the reaction is conducted in a gas phase.

6. The method of producing a carbonic diester according to claim 5 wherein the amount of carbon monoxide per mole of the alcohol is within the range of 0.1 to 1000 moles.

7. The method of producing a carbonic diester according to claim 5 wherein the amount of oxygen per mole of the alcohol is within the range of 0.001 to 2 moles.

8. The method of producing a carbonic diester according to claim 1 which comprises allowing an alcohol of 1 to 6 carbon atoms to react with carbon monoxide and oxygen in proportions of 0.1 to 1000 moles and 0.001 to 2 moles per mole of the alcohol respectively, in a gas phase at the temperature of 50 to 200° C. and under the pressure of 1 to 50 atm and in the presence of the catalyst wherein the catalyst component is selected from the group consisting of copper halide, a salt of copper with an inorganic weak acid, a salt of copper with an organic acid and a complex formed with one of these compounds supported on a support, wherein said support is an activated carbon with a specific surface area of 700 to 3000 $m^2/g$, obtainable from a vegetable or polymer raw material and (i) said activated carbon is substantially free from aluminum or if it contains aluminum, the aluminum content of said activated carbon is greater than 0 up to 1% by weight, and (ii) said activated carbon is substantially free from sulfur or if it contains sulfur, the sulfur content of said activated carbon is greater than 0 up to 0.7% by weight.

9. The method of producing a carbonic diester according to claim 8 wherein the alcohol is methanol.

10. A method of producing a carbonic diester which comprises allowing an aliphatic alcohol having 1 to 6 carbon atoms to react with carbon monoxide and oxygen in the presence of a catalyst which comprises a copper compound supported on an activated carbon, wherein said activated carbon is an activated carbon with a specific surface area of 700 to 3000 $m^2/g$ obtainable from a vegetable or polymeric raw material and (i) said activated carbon is substantially free from aluminum or if it contains aluminum, the aluminum content of said activated carbon is greater than 0 up to 2% by weight, and (ii) said activated carbon is substantially free from sulfur or if it contains sulfur, the sulfur content of said activated carbon is greater than 0 up to 1% by weight.

11. The method according to claim 10, wherein the activated carbon is obtained from a vegetable material which comprises coconut shells.

12. The method of producing a carbonic diester according to claim 1, wherein the raw material of the activated carbon is comprised of carbonizable seed shells or a carbonizable polymer.

13. The method of producing a carbonic diester according to claim 1, wherein the carbonizable polymer is selected from the group consisting of phenol resin, furan resin, epoxy resin, acrylic resin, polyacrylonitrile, vinylidene chloride resin, rayon and cellulose.

14. The method of producing a carbonic diester according to claim 1, wherein the support is chlorinated at a high temperature to reduce the aluminum content.

15. The method of producing a carbonic diester according to claim 1, wherein the support is alkali-washed to reduce the sulfur content.

16. The method of producing a carbonic diester according to claim 1, wherein said activated carbon is substantially free from sulfur or if it contains sulfur, the sulfur content of said activated carbon is greater than 0 up to 0.7% by weight.

17. The method of producing a carbonic diester according to claim 1, wherein (i) said activated carbon is substantially free from aluminum or if it contains aluminum, the aluminum content of said activated carbon is greater than 0 up to 1% by weight and (ii) said activated carbon is substantially free from sulfur or if it contains sulfur, the sulfur content of said activated carbon is greater than 0 up to 0.7% by weight.

18. The method of producing a carbonic diester according to claim 1, wherein the copper compound is selected from the group consisting of copper halide, a salt of copper with an inorganic weak acid, a salt of copper with an organic acid and a complex formed with one of said salts.

19. A method of producing a carbonic diester according to claim 1, wherein the amount of the catalyst component to be supported is within the range of 0.5 to 80% by weight based on the weight of the support.

20. A method of producing a carbonic diester according to claim 1, wherein the catalyst component is selected from the group consisting of copper halide, a salt of copper with an inorganic weak acid, a salt of copper with an organic acid, and a complex formed with one of them and is supported, in a proportion of 0.5 to 80% by weight based on the total weight of the support on an activated carbon with a specific surface area of 700 to 3,000 $m^2/g$, obtained from carbonizable seed shells or a carbonizable polymer, wherein (i) said activated carbon is substantially free from aluminum or if it contains aluminum, the aluminum content of said activated carbon is greater than 0 up to 1% by weight and (ii) said activated carbon is substantially free from sulfur or it contains sulfur, the sulfur content of said activated carbon is greater than 0 up to 0.7% by weight.

21. A method of producing a carbonic diester which comprises allowing an aliphatic alcohol of 1 to 6 carbon atoms to react with carbon monoxide and oxygen in the presence of a catalyst consisting essentially of a copper compound supported on a support, wherein said support is an activated carbon with a specific surface area of 700 to 3,000 $m^2/g$ obtainable from a vegetable or polymer raw material with a proviso that (i) said activated carbon is substantially free from aluminum or the aluminum content of said activated carbon is greater than 0 up to 2% by weight and (ii) said activated carbon is substantially free from sulfur or the sulfur content of said activated carbon is greater than 0 up to 1% by weight.

22. A method of producing a carbonic diester according to claim 21, wherein the reaction is conducted in a gas phase.

23. A method of producing a carbonic diester according to claim 1, wherein said activated carbon is substantially free from aluminum or, if it contains carbon, the aluminum content of said activated carbon is greater than 0 up to 1% by weight.

24. A method of producing a carbonic diester according to claim 1, wherein the catalyst is a copper compound selected from the group consisting of cuprous chloride, cupric chloride, copper borate, copper acetate, copper oxalate, and a complex formed with one of said compounds.

25. A method of producing a carbonic diester according to claim 1, wherein said alicyclic alcohol is cyclohexanol.

* * * * *